(12) United States Patent
Elmstrom

(10) Patent No.: US 6,355,865 B1
(45) Date of Patent: Mar. 12, 2002

(54) POLLENIZER PLANTS FOR USE IN THE PRODUCTION OF SEEDLESS WATERMELON

(75) Inventor: Gary W. Elmstrom, Woodland, CA (US)

(73) Assignee: Sunseeds, Inc., Morgan Hill, CA (US)

( * ) Notice: Subject to any disclaimer, the term of this patent is extended or adjusted under 35 U.S.C. 154(b) by 0 days.

(21) Appl. No.: 09/320,515

(22) Filed: May 26, 1999

(51) Int. Cl.[7] ............ A01H 1/02; A01H 1/04; A01H 5/00; A01H 1/08; A01H 5/08
(52) U.S. Cl. ............ 800/308; 800/260; 800/271; 800/274
(58) Field of Search ............ 800/308, 298, 800/260, 271, 274

(56) References Cited

U.S. PATENT DOCUMENTS

| | | | |
|---|---|---|---|
| 5,007,198 A | 4/1991 | Gray et al. | 47/58 |
| 5,628,145 A | * 5/1997 | Beversdorf et al. | 47/58 |
| 5,877,400 A | 3/1999 | Tomes et al. | 800/205 |

FOREIGN PATENT DOCUMENTS

| | | |
|---|---|---|
| WO | WO 98/49888 | 11/1998 |

OTHER PUBLICATIONS

Hodges. Growing Seedless (Triploid) Watermelon, Neb-Facts, Nebraska Cooperative Extension NF94–127, 3 pp., 1994.*

Maynard et al. Triploid watermelon production practices and varieties. Acta Horticulturae. vol. 318, pp. 169–178. 1992.*

Mussen. Apiculture News, UC Davis Department of Entomology, 10 pp. Mar. 1999.*

USDA, ARS, National Genetic Resources Program, Germplasm Resources Infomation Network (GRIN) [Onlilne Database] National Germplasm Resources Laboratory, Beltsville, Maryland. http://www.ars–grin.gov, 1997.*

Maynard D., Growing Seedless Watermelons, H.S. 687, 1996.

* cited by examiner

*Primary Examiner*—David T. Fox
(74) *Attorney, Agent, or Firm*—Frommer Lawrence & Haug LLP

(57) ABSTRACT

This invention relates to a pollenizer watermelon plant, for use in the production of seedless watermelon. The pollenizer plant is characterized by at least two of the following features: (a) distinguishable fruit phenotype; (b) high number of male flowers; (c) continued flowering; (d) early flowering; and/or (e) modified plant morphology and growth habit. The invention particularly relates to plants having the characteristics of plants grown from the seed deposited at the ATCC under ATCC accession number 203691. The invention further relates to plants obtainable by propagation of, and/or breeding with a watermelon plant grown from the seed deposited at the ATCC under ATCC accession number 203961.

10 Claims, No Drawings

POLLENIZER PLANTS FOR USE IN THE PRODUCTION OF SEEDLESS WATERMELON

FIELD OF INVENTION

This invention relates to a pollenizer watermelon plant, for use in the production of seedless watermelon.

The pollenizer plant is characterized by at least two of the following features: (a) distinguishable fruit phenotype; (b) high number of male flowers; (c) continued flowering; (d) early flowering; and/or (e) modified plant morphology and growth habit.

The invention particularly relates to plants having the characteristics of plants grown from the seed deposited at the ATCC under ATCC accession number 203961. The invention further relates to plants obtainable by propagation of, and/or breeding with a watermelon plant grown from the seed deposited at the ATCC under ATCC accession number 203961.

All documents cited herein are hereby incorporated herein by reference.

BACKGROUND OF THE INVENTION

Fruit of standard seeded watermelon varieties may contain as many as 1,000 seeds in each fruit. Hybrid seedless (triploid) watermelons have been grown for over 40 years in the United States. However, it was not until recently that improved varieties, aggressive marketing, and increased consumer demand created a rapidly expanding market for seedless watermelons.

The seedless condition in watermelon actually results from a cross between two plants of incompatible chromosome complements. The normal chromosome number in most living organisms is referred to as "2N". Seedless watermelons are produced on sterile triploid ("3N") plants, which result from crossing a normal seeded diploid (2N) plant with a tetraploid ("4N"). Tetraploid parental lines are usually developed by treating diploid plants with colchicine, which induces a doubling of the chromosome number.

To produce a harvest of seedless watermelons, the triploid plants must be interplanted with a pollenizer variety ("2N"). As the pollen from the triploid plants is sterile and unable to stimulate fruit set, pollen from fertile diploid plants must be provided. In the U.S., growers generally use Allsweet type hybrids as a pollen source as these provide themselves marketable fruit. The commercial seedless (triploid) plants and the pollenizer variety are normally seeded in separate flats and transplanted after about 4 weeks to the field. Close interplanting between triploid plants and pollenizers is required to enable bees to transfer sufficient pollen to the triploid plants, as inadequate pollination results in seedless fruit that are triangular in shape and of poor quality. Most growers place the pollenizer plants in every third row (to aid in harvesting) or every third plant in the row. This will lead to a field wherein two thirds of the fruit is seedless and one-third of the fruit is seeded. Usually, the pollenizer variety is selected to produce fruit that is distinguishable from the seedless variety, to avoid mixing of the seeded and seedless fruit after harvest.

Inter-planting of plants producing seeded with plants producing seedless fruit in the same field has significant agronomical drawbacks. First, the two different types of plants grow at different rates and the timing of water and fertilizer application for the two varieties often is not synchronized. Maturity dates also vary so that multiple harvests must be used. More importantly, the difference in development can cause problems as it is crucial that pollen from the diploid pollenizer is available when the female blossoms on the triploid plant are open and ready for pollination. This is complicated by the fact that diploid plants producing seeded fruit stop flowering once they have set fruit, so that pollen is no longer available for seedless fruit development.

SUMMARY OF THE INVENTION

The invention relates to a pollenizer watermelon plant, for use in the pollination of triploid watermelon plants in the production of seedless watermelon. The pollenizer plant of the invention is characterized by at least two, preferably three, more preferably four, most preferably five of the following features:

a) distinguishable fruit phenotype;

b) high number of male flowers;

c) continued flowering;

d) early flowering; and/or e) modified plant morphology and growth habit.

The invention particularly relates to a pollenizer plant characterized by at least two, preferably three, more preferably four, most preferably five of the following features: fruit produced on the plant weighs less than 5 lbs. each and/or is less than 15 cm in diameter; at least 20 male flowers are grown per plant per day during triploid flowering period; fruit set does not halt flowering, male flowers open at least 10 minutes earlier than commercial triploid plants; a diameter of the vine that is 65% or less of the diameter of a commercial diploid plant and/or a prostrate growth habit.

These features may be present in the pollenizer plant of the invention, in any and all possible combinations; any two, three, four or five of the features may be present in any possible combination. For example, the plant may have a distinguishable fruit phenotype together with a high number of male flowers, and/or continued flowering, and/or early flowering, and/or modified plant morphology and growth habit; all other combinations of two, three, four or five of the features are possible and are meant to be included in the invention.

The invention preferably relates to a pollenizer plant characterized by a distinguishable fruit phenotype, a high number of male flowers and continued flowering.

The invention particularly relates to the seed deposited at ATCC under ATCC accession number 203961, a plant which is grown from this seed, and cells or tissues from a plant grown from this seed. The invention further relates to plants obtainable by propagation of, and/or breeding with a watermelon plant grown from the seed deposited at the ATCC under ATCC accession number 203961.

The invention further relates to plant parts and seeds of such pollenizer plants described above.

The invention furthermore relates to a method for producing seedless watermelon, which comprises interplanting seeds or plants of a triploid watermelon line with seeds or plants of the pollenizer line of the invention, and allowing the pollen of these pollenizer plants to pollinate the triploid watermelon plants, so as to stimulate fruitset thereon.

Preferably, seeds or plants of a triploid watermelon line are interplanted with seeds or plants of the pollenizer line of the invention, in specific patterns in the field, whereby these pollenizer plants grow in close proximity to the triploid watermelon plants.

The invention furthermore relates to a method for producing seedless watermelon, whereby seeds of a triploid watermelon line are blended with seeds of the pollenizer fine of the invention prior to sowing.

The invention further relates to a system for producing seedless watermelon which comprises:

seeds capable of growing into triploid watermelon plants, or the plants grown therefrom, and, seeds capable of growing into the pollenizer plants characterized as described above, or the plants grown therefrom.

DETAILED DESCRIPTION OF THE INVENTION

Seedless fruit as used herein refers to fruit containing few (less than 5% of seeded fruit which contains at least 500 seeds) or no normal seeds. It is possible that the fruit from the first fruit settings of a seedless plant will contain some (up to 20/fruit) seeds. Also, some varieties designated as "seedless" may contain rudimentary, edible seeds or seed coats. Plants that carry seedless or seeded fruit will also be referred to as seedless or seeded plants, respectively.

As used herein diploid ("2N"), triploid ("3N") and tetraploid ("4N") refers to the number of chromosomes in all or in at least the majority of cells in the plant. For the cultivation of seedless watermelon referred to herein, triploid plants are used as female parent plants (for fruit set), while diploid plants are used as the male parent plants (providing pollen).

As used herein, the term "comprising" means "including".

The term "pollenizer" or "pollenizer plant" refers to a plant that is used to provide pollen for fruit set on suitable female parent plants, preferably triploid plants, and is also referred to as the male parent plant. This does not exclude that the pollenizer can also self-pollinate and set fruit. A number of measures are taken to ensure that pollen from the pollenizer plant can indeed pollinate the plant on which fruit set is to occur, such as, but not limited to, adequate interplanting and providing an adequate bee population.

A commercial diploid pollenizer line (or plant of such a line) as used herein refers to inbred or hybrid lines which are commercially used at the time of the present invention as pollenizers in the production of seedless watermelon. These lines are generally selected based on the marketability of the (seeded) fruit produced on the plants. For the purposes of this invention, representative examples of commercial diploid pollenizer lines are Calsweet, Sangria and Royal Sweet. These commercial diploid lines are all comparable with regard to fruit phenotype, number of male flowers, start and duration of flowering and plant morphology and growth habit.

The terms commercial triploid watermelon plants and commercial seedless watermelon as used herein refer to the seedless plants and fruits marketed. These seedless plants yield seedless fruit as defined herein. Usually, the seedless fruit has a diameter of at least 15 cm and/or a weight of at least 10 lbs. when harvested.

The pollenizer plants of the present invention display certain characteristics, which provide specific advantages for their use as pollenizer plants in the production of seedless watermelon. The characterizing features, which are evaluated, are as follows:

a) Distinguishable Fruit Phenotype

Distinguishable fruit phenotype refers to the fact that the phenotype of the fruit differs from that of the commercial seedless watermelon produced by commercial seedless triploid plants, in a way that can easily be established. Preferably, this phenotype is measurable in weight and/or size. More preferably, the fruit produced by the pollenizer plants of the present invention weighs less then ten, most preferably less than five lbs., especially preferably less than four lbs. each. Additionally or alternatively, the diameter of the fruit produced on the pollenizer plant of the invention is less than 15 cm, preferably less than 12 cm, more preferably less than 10 cm, most preferably less than 8 cm in diameter on average. The difference in fruit phenotype between that the seedless fruit and that of the pollenizer plant of the invention can optionally be increased by a difference in color or rind pattern. As commercial seedless watermelon is in many cases striped, the pollenizer plant of the invention preferably produces fruit with a distinguishable rind pattern. Alternatively, the difference in phenotype can be a difference in shape.

b) High Number of Male flowers

The number of male (staminate) flowers refers to the number of male flowers present on a pollenizer plant per day, during the blooming period of the female blossoms of the triploid plant, hereinafter also referred to as "triploid blooming period" (plants of diploid watermelon lines will generally start producing flowers 7 to 10 days before the female blossoms of triploid watermelon lines start to open, but these days are not taken into account as no pollination of triploid flowers can occur during this time). The number of male flowers on the pollenizer plant of the invention is preferably at least 20, more preferably 30, especially preferably 40, most preferably 50 flowers per plant per day during the triploid blooming period. Alternatively, the number of flowers can be expressed as compared to commercial diploid lines and will preferably be at least twice, more preferably three times, especially preferably four times, most preferably five times (or more) the number of male flowers produced on a commercial diploid line.

c) Continued Flowering

In commercial diploid watermelon lines the start of fruit set on some of the flowers will stop the flowering on the rest of the plant. The pollenizer plants of the invention are preferably characterized in that they will continue to produce male flowers, even after fruit set has started.

d) Early Flowering

Male flowers on commercial diploid lines open at the same time or slightly later than the female triploid blossoms. The characteristic of early flowering (or anthesis) of the pollenizer plant of the invention can thus be determined relative to that of either commercial diploid pollenizer plants or commercial triploid watermelon plants. Preferably the flowers of the pollenizer of the invention will start to open at least 10 minutes, more preferably at least 15 minutes, especially preferably at least 20 minutes, most preferably 30 minutes or more before the female blossoms of the triploid watermelon (or a commercial diploid pollenizer) open and are receptive to pollen.

e) Modified Plant Morphology and Growth Habit

The morphology and growth of the pollenizer plants of the invention is preferably characterized by one or more of a number of features which differ from those of commercial diploid pollenizer lines. Standard commercial diploid pollenizer plants display a plant morphology and growth which is similar to that of a triploid plant, or are only slightly more slender in stem diameter. The pollenizer plants of the invention preferably have remarkably more slender vines and runners, more preferably the diameter of the vines will be less than 75%, most preferably less than 65%, especially preferably 50% or less than the diameter of the vines of a triploid watermelon plant in the same stage of development. Additionally or alternatively, the pollenizer plant will preferably display an overall prostrate growth. Additionally, the flowers of the pollenizer plant of the invention can display an altered morphology, such as a color difference, which makes them more attractive to visiting insects.

Interplanting refers to the combination of two or more types of seeds or plants sown or transplanted on a field. As watermelon fruit set and enlargement is dependent upon growth regulators from the pollen grains and from embryos in developing seeds within the fruits, adequate pollination is important for quality and quantity of the fruit. Interplanting can occur at random, by mixing seeds before sowing, or can be the result of a specific field arrangement of seeds or transplanted plantlets.

Maynard "Growing Seedless Watermelons", HS 687, March 1996, relates to examples of field arrangements which have been used successfully for the production seedless watermelon using standard current practice. The field arrangements can be obtained by direct sowing of seeds in the field or by transplanting seeds grown in separate flats.

Interplanting of commercial diploid and triploid lines is usually done at a ratio of 1:2, to ensure adequate pollination of the triploid flowers. The pollenizer plant of the present invention can also be interplanted with a commercial triploid line at a 1:2 ratio. However, since the pollenizer of the invention has more male blossoms and is more slender and less competitive, adequate pollination of the triploid plants can be obtained when interplanting occurs at a lower ratio (1:3 to 1:5, or less).

Cross-pollination as used herein refers to the pollination of the flowers of the female (preferably triploid) parent plants with pollen from the flowers of a pollenizer plant which leads to the production of seedless fruit.

An object of the present invention is to increase the number of seedless fruit produced per acre in a field. The use of the pollenizer of the invention allows a higher triploid population per acre and increased pollination efficiency resulting in higher yield of seedless fruit and thus increased income for the grower.

According to the present invention, pollenizer plants are obtained which can be used in, and provide important advantages for, the production of seedless watermelon. The plants of the invention are characterized by at least two, preferably three, more preferably four, most preferably five of the characteristics selected from the group consisting of: distinguishable fruit phenotype, high number of male flowers, continued flowering, early flowering, and modified plant morphology and growth habit.

These characteristics directly or indirectly provide advantages for the use of the pollenizer plant of this invention in the production of seedless watermelon. The production of easily distinguishable fruit by the pollenizer line facilitates the harvesting of fruit. The pollenizer plant of this invention may produce fruit which is small and in fact unmarketable, eliminating all need for a separate harvest or separation of the seedless and seeded fruit after harvest.

As the pollenizer plant of this invention preferably produces large numbers of male blossoms, it can provide more pollen for fruit set on female parent plants. Both by the number of flowers and/or their morphology (including flower color), this plant is preferably more attractive to bees than the commercial diploid pollenizers, which also stimulates pollination. Preferably, the start of fruit set does not affect flowering on the pollenizer plant of this invention, which means that it is capable of providing pollen over a longer period of time. Furthermore, flowering will preferably occur earlier on the pollenizer plant of the invention than on the female parent (triploid) plants, which is advantageous for cross-pollination of the female parent plants, as this ensures that bees will be carrying pollen from the pollenizer line by the time the flowers on the female parent plant open. The runners on the pollenizer plant of this invention are preferably long and slender which places its male flowers in closer proximity to the flowers on the seedless plants. Also, the pollenizer plant of this invention is preferably more slender, allowing it to be more invasive while less competitive to the female (triploid) parent plants. This makes it possible to more closely interplant the pollenizer of the invention with the triploid line, allowing better cross-pollination conditions, without negatively affecting development or fruit set of the seedless plants.

The use of the pollenizer of the present invention in the production of seedless watermelon thus can provide the following important advantages, as compared to commercial diploid pollenizers, for the grower:

1) The possibility to increase the number of triploid plants (or other female plants) per acre will result in an increased number of seedless fruit harvested per acre, resulting in higher income to the grower because these sell for a premium price.

2) A longer production period due to the fact that the pollenizer plants of this invention continue to produce male blossoms and pollen much longer than commercial diploids, also positively influencing seedless fruit yield.

3) Improved fruit set because the flowers on the pollenizer plants are more attractive to bees, the long runners on these plants intermingle better with the seedless plants, and the plants produce more male blossoms than standard diploid pollenizers. This again will positively affect yield of seedless fruit.

4) Growers can grow fields from which exclusively seedless fruit is harvested. This eliminates problems of mixing with seeded fruit.

Secondary, but also significant advantages can be:

5) Harvesting costs are reduced since the grower no longer has to harvest when the seeded fruit are ready and again when the seedless fruit are ready.

6) Production practices can be optimized since the grower is not having to compromise some practices because of different growth rates for seeded and seedless plants.

A preferred embodiment of the invention is a pollenizer plant characterized by the following features: a) distinguishable fruit phenotype, b) high number of male flowers, c) continued flowering, d) early flowering and e) modified plant morphology and growth habit.

An especially preferred embodiment of the invention is a pollenizer plant characterized by the fact that the fruit produced on the plant weighs less than 5 lbs. each and/or is less than 15 cm in diameter, that it produces at least 20 male flowers per plant per day during triploid flowering period, that fruit set does not halt flowering, that its male flowers open at least 10 minutes earlier than commercial triploid plants, and that the diameter of its vines is 65% or less the diameter of a commercial diploid plant.

Plants according to the preferred embodiment of the invention can be obtained form the seeds deposited at the ATCC under ATCC accession number 203961. Such plants can further be propagated to produce more plants with the same characteristics.

EXAMPLES

The invention will be further described by the following examples.

1. Development of a Pollenizer Line

A USDA germline was selfed for several generations (Drs. Graves Gillaspie and Robert Jarret of the USDA Plant Genetic Resources Conservation Unit in Experiment, Georgia).

From this line, a selection for a pollenizer line was made based on a number of characteristics including fruit phenotype, number of male blossoms, flowering time and duration, and plant competitiveness. The plants from the selected line produce large numbers of male blossoms (up to 5 times the number produced by commercial diploid plants), and anthesis occurs at least 10 minutes before the triploid plants. They produce small, unmarketable fruit, but fruit set on the plant does not inhibit further male flower production. The plants themselves are slender and not as competitive in the field as commercial diploid varieties.

Seed of the selected pollenizer line was deposited as pollenizer 1 at the ATCC under ATCC accession number 203961.

2. Testing of Pollenizer Line For the Production of Seedless Watermelon a) Efficiency as Pollenizers A field trial was set up to investigate whether the pollenizer line selected in Example 1 could provide adequate pollination for the production of seedless watermelon.

Separate plots of 45 feet wide (9 rows) by 70 feet long, separated from each other by 30 feet in each direction, were used. Triploid (Revolution) plants were interplanted with either a commercial diploid line (Maya) or with the pollenizer selected in Example 1, every third row (set-up 1 and 3), every third plant (set-up 2 and 4), every fourth plant (set-up 5) or every sixth plant (set-up 6). Spacing between plants was 36, 30, 27 or 24 inches. The number of plants for each set-up is detailed in Table 1. Every set-up was tested in at least two plots.

TABLE 1

| Set-up | Number of Plants | | | | Plant Interspacing (Inches) |
| --- | --- | --- | --- | --- | --- |
| | Triploid (Revolution) | Diploid (Maya) | Selected Pollenizer-1 | Total | |
| 1 | 1936 | 968 | 0 | 2904 | 36 |
| 2 | 1936 | 968 | 0 | 2904 | 36 |
| 3 | 1936 | 0 | 968 | 2904 | 36 |
| 4 | 2904 | 0 | 1452 | 4356 | 24 |
| 5 | 2904 | 0 | 968 | 3872 | 27 |
| 6 | 2904 | 0 | 580 | 3484 | 30 |

Fruit was harvested from triploid and diploid (Maya) plants. The average number of seedless fruit harvested (from two replications) is listed below.

| Set-Up | Seedless Fruit |
| --- | --- |
| 1 | 3974 |
| 2 | 4126 |
| 3 | 5037 |
| 4 | 5368 |
| 5 | 5120 |
| 6 | 4444 | comparison of the fruit set on triploid plants, for those plots where triploid plants were interplanted with either diploid plants of a commercial variety or with the pollenizer 1 plants in the same number (set-up 1 and 2 with set-up 3), indicates that the pollenizer plants selected in Example 1 are indeed better pollenizers, as the average fruit set on the triploid plants is increased 24%. As these pollenizer plants are less competitive, less space is needed for interplanting and the number of triploid and pollenizer plants per plot can be increased, which also positively effects the number of seedless fruit obtained (set-up 4).

The experiment demonstrates that interplanting of commercial triploid plants with the pollenizer plants of the present invention at a 2:1 ratio provides adequate fruit set.

Additional experiments using lower ratios of triploid plants demonstrate that due to the higher number of male flowers on the pollenizer plants of Example 1, interplanting of commercial triploid plants with the pollenizer of the present invention at lower ratios (1:3, 1:4, 1:5) still ensures adequate fruit set on the triploid plants.

The commercial diploid lines used in current standard practice also set (seeded) fruit, while the pollenizer selected in Example 1 does not set marketable fruit. Thus, the total number of fruit produced, and thus the yield of the field is affected by use of the selected pollenizer.

The obtained total yield in pounds of marketable fruit using the selected pollenizer of Example 1 will generally be lower than the yield obtained with the commercial pollenizer line. However, as the value on the market of the seedless fruit obtained from the triploid plant well exceeds the value of the seeded fruit obtained from the diploid plant, the revenue for the grower is about the same. However, factors such as not having to separate seeded from seedless fruit, harvesting fewer times, handling fewer fruit per acre, having to market only one type of fruit rather than two, and using fewer packing cartons, have an important impact on production cost. Consequently, the net return per acre using the selected pollenizer of Example 1 will be significantly higher.

3. Detailed Evaluation of the Characteristics of the Pollenizer Line Selected in Example 1 and the Influence of These Characteristics on the Use of Such Pollenizer Plants in Seedless Watermelon Production Field trials were conducted to compare different characteristics of the pollenizer selected in Example 1 and the effect of these characteristics in the production of seedless watermelons. Comparative data were collected to determine pollen compatibility, flower production, pollen production, anthesis period, bee visitation, anther morphology and pollen viability of the pollenizer line selected in Example 1, as compared to commercial pollenizers.

a) Pollen Compatibility

The object of the study was to determine the effect of pollen of the pollenizer line of Example 1 on triploid fruit set and fruit quality (fruit weight, percent soluble solids and incidence and severity of hollowheart) in comparison to commercial pollenizers. Cross-pollination was done using controlled hand pollination.

No differences were observed in triploid fruit set and fruit quality between using pollen of the selected pollenizer line and using pollen of a commercial pollenizer line.

b) Flower Production

The number of male flowers produced by the pollenizer of Example 1 during peak blooming period was compared to the number of male flowers produced by commercial pollenizer lines. Random samples were taken from plants during the period of blooming of the triploid plants. It was observed that the pollenizer plants selected in Example 1 produced on average 6 times as many staminate flowers (upwards of 50 male flowers/plant/day) as the commercial diploids (less than 10 male flowers/plant/day).

c) Pollen Production

The average number of pollen grains produced per staminate flower by a plant of the pollenizer line selected in Example 1, is compared to that of standard commercial pollenizers. Random sampling is performed of staminate flowers during triploid blooming period.

It is established that the average number of pollen grains produced by a flower from the selected pollenizer line (of Example 1) is similar or higher to that obtained from a plant of a commercial pollenizer line.

d) Anthesis Period

The anthesis period of flowers of a plant of the pollenizer line of Example 1 was evaluated in relation to anthesis on the triploid plants and in comparison to anthesis or commercial diploid lines used as pollenizers. It was observed that the flowers of the selected pollenizer plants reached anthesis before all other cultivars examined (up to 30 minutes earlier). This "earliness" in pollen presentation will facilitate pollen deposition of viable pollen onto triploid stigmata.

e) Bee Visitation

The attractiveness of the flowers of a plant of the pollenizer line selected in Example 1 to pollinators (bees) was compared to that of other (commercial) pollenizers. This was evaluated visually at intervals during anthesis. Foraging bee concentrations on flowers of the selected pollenizer line were consistently greater than those found on other cultivars being evaluated.

f) Anther Morphology

The morphology of anthers of the flowers of the pollenizer line selected in Example 1 was investigated and found to differ from that of standard commercial diploid lines. The influence of the anther morphology on pollen removal by pollinating insects was investigated. Staminate flowers were exposed to pollinators and pollen remaining on the stigmas after insect visitation was quantified. It is observed that the amount of pollen on the stigmas of flowers pollinated by the selected pollenizer plants is similar or increased to that on flowers pollinated by other cultivars.

g) Pollen Viability

The duration of pollen viability of the pollenizer line selected in Example 1 is compared to that of commercial diploid lines using biological staining procedures. It is established that the duration of viability for pollen from plants of the selected pollenizer line is similar to that for pollen of plants of commercial diploid lines.

Other modifications of the present invention will be apparent to those skilled in the art without departing from the scope of the present invention.

What is claimed is:

1. In a process for producing seedless watermelon, comprising
    a) interplanting plants or seeds from a triploid plant line with pollenizer plants and
    b) allowing pollination of said triploid plants with pollen from flowers of said pollenizer plants, wherein the improvement comprises said pollenizer plants being plants which produce unmarketable fruit, distinguishable in fruit shape and/or size, or the seeds thereof from the triploid plants, and the
    c) harvesting is only of the fruits from said triploid plants and not any fruit from the pollenizer plants.

2. The process of claim 1, wherein said seeds of said triploid plant line and said pollenizer line are interplanted by mixing of said seeds before sowing.

3. The process of claim 1, wherein said seeds of said triploid plant line and said pollenizer line are interplanted by sowing said seeds in specific field patterns.

4. The process of claim 1, wherein said plants of said triploid plant line and the pollenizer line are interplanted by transplanting flats of the seeds grown separately in specific field patterns.

5. The process of claim 1, characterized in that the fruit grown on said pollenizer plant weights less than 5 lbs.

6. The process of claim 1, characterized in that the fruit grown on said plant is less than 12 cm in diameter.

7. The process of claim 1, characterized in that the number of male flowers grown on said pollenizer plant during triploid flowering period is at least 20 flowers per plant per day.

8. The process of claim 1, characterized in that the diameter of the vines is less than 65% of that of the commercial triploid plant.

9. A method for harvesting 100% seedless watermelon, said method comprising:
    1) interplanting
        a) pollenizer plants characterized in that they produce unmarketable fruit, distinguishable from the seedless watermelon in fruit shape and/or size, or seeds of said pollenizer
    with
        b) commercial triploid parent plants or seeds thereof: and
    2) harvesting only the fruit produced on said commerical triploid parent plants, thus obtaining 100% seedless fruit.

10. A process for producing seedless watermelon, said process comprising
    a) interplanting plants or seeds from a triploid plant line with pollenizer plants which produce unmarketable fruit, distinguishable in fruit shape and/or size, or the seeds thereof, wherein said pollenizer plant or seed is a plant or seed which is grown from the seed deposited at the ATCC under ATCC accession number 203961,
    b) allowing pollination of said triploid plants with pollen from flowers of said pollenizer plants, and
    c) harvesting only the fruits from said triploid plants.

* * * * *

UNITED STATES PATENT AND TRADEMARK OFFICE
CERTIFICATE OF CORRECTION

PATENT NO.   : 6,355,865 B1
DATED        : March 12, 2002
INVENTOR(S)  : Gary W. Elmstrom It is certified that error appears in the above-identified patent and that said Letters Patent is hereby corrected as shown below:

<u>Title page,</u>
Item [73], Assignee: please delete "Sunseeds, Inc.", and replace it with -- Sunseeds Company --

Signed and Sealed this

Eighteenth Day of February, 2003

JAMES E. ROGAN
*Director of the United States Patent and Trademark Office*